US008814798B2

(12) United States Patent  (10) Patent No.: US 8,814,798 B2
Corbucci et al.  (45) Date of Patent: Aug. 26, 2014

(54) IMPLANTABLE DEVICE AND METHOD FOR MONITORING VENOUS DIAMETER

(75) Inventors: Giorgio Corbucci, Cento (IT); Josephus P. A. Smit, Arnhem (NL); Johannes S. Van Der Veen, Dieren (NL); Geert Van Lembergen, Merchtem (BE); Marinus C. J. Verschelling, Amersfoort (NL)

(73) Assignee: Medtronic, Inc., Minneapolis, MN (US)

( * ) Notice: Subject to any disclaimer, the term of this patent is extended or adjusted under 35 U.S.C. 154(b) by 1638 days.

(21) Appl. No.: 12/109,408

(22) Filed: Apr. 25, 2008

(65) Prior Publication Data

US 2009/0270729 A1  Oct. 29, 2009

(51) Int. Cl.
*A61B 5/0205* (2006.01)
*A61B 5/053* (2006.01)
*A61B 8/08* (2006.01)
*A61B 5/107* (2006.01)
*A61B 5/0215* (2006.01)

(52) U.S. Cl.
CPC ............ *A61B 5/0205* (2013.01); *A61B 5/1076* (2013.01); *A61B 5/02152* (2013.01)
USPC ........... 600/438; 600/484; 600/486; 600/547; 600/309; 600/325

(58) Field of Classification Search
None
See application file for complete search history.

(56) References Cited

U.S. PATENT DOCUMENTS

| 4,721,113 | A | 1/1988 | Stewart et al. |
| 4,774,950 | A | 10/1988 | Cohen |
| 5,020,541 | A | 6/1991 | Marriott |
| 5,040,540 | A | 8/1991 | Sackner |
| 5,129,394 | A | 7/1992 | Mehra |
| 5,163,429 | A | 11/1992 | Cohen |
| 5,184,621 | A | 2/1993 | Vogel et al. |
| 5,935,066 | A | 8/1999 | Harris |
| 6,471,872 | B2 | 10/2002 | Kitaevich et al. |
| 6,600,949 | B1 | 7/2003 | Turcott |
| 6,610,015 | B2 | 8/2003 | Caterini et al. |
| 6,666,826 | B2 | 12/2003 | Salo et al. |
| 6,741,885 | B1 | 5/2004 | Park et al. |
| 6,752,765 | B1 | 6/2004 | Jensen et al. |
| 6,802,811 | B1 * | 10/2004 | Slepian ......................... 600/309 |
| 7,118,534 | B2 | 10/2006 | Ward et al. |
| 7,160,252 | B2 | 1/2007 | Cho et al. |
| 2004/0249297 | A1 | 12/2004 | Pfeiffer et al. |
| 2005/0049511 | A1 | 3/2005 | Warring-Davies |
| 2005/0203434 | A1 | 9/2005 | Kassab |
| 2006/0056161 | A1 * | 3/2006 | Shin et al. ..................... 361/749 |
| 2007/0088214 | A1 * | 4/2007 | Shuros et al. ................. 600/437 |
| 2007/0156193 | A1 | 7/2007 | Cho et al. |

FOREIGN PATENT DOCUMENTS

| DE | 10 2005 035022 | 11/2006 |
| EP | 1635158 | 3/2006 |
| WO | WO 2004075928 | 9/2004 |
| WO | WO 2006084156 | 8/2006 |
| WO | 2006102905 | 10/2006 |

OTHER PUBLICATIONS

Vinayak et al, Usefulness of the External Jugular Vein Examination in Detecting Abdominal Central Venous Pressure in Critically Ill Patients, Arch Intern Med., Oct. 23 2006, 2132-2137, vol. 166.
(PCT/US2009/040633) PCT Notification of Transmittal of the International Search Report and the Written Opinion of the International Searching Authority.

* cited by examiner

*Primary Examiner* — Shafiqul Haq
(74) *Attorney, Agent, or Firm* — Carol F. Barry (57) ABSTRACT

An implantable medical device system and associated method receive a signal from an implantable sensor operatively positioned relative to a vein, the signal being responsive to changes in a diameter of the vein. A diameter of the vein is determined in response to the sensor signal and used in estimating central venous pressure (CVP).

15 Claims, 11 Drawing Sheets

IMPLANTABLE DEVICE AND METHOD FOR MONITORING VENOUS DIAMETER

TECHNICAL FIELD

The invention relates generally to implantable medical devices and, in particular, to a device and method for monitoring central venous pressure based on vein diameter measurements.

BACKGROUND

Central venous pressure (CVP) increases with worsening heart failure. As CVP increases, vein diameter increases. During clinical examination of heart failure patients, echocardiography can be used to monitor vein diameter as an indicator of CVP. Diagnosis of high CVP is useful in managing the treatment of heart failure patients. Implantable medical devices are available or have been proposed for providing ambulatory monitoring of physiological signals associated with heart failure, such as intracardiac blood pressure, heart rhythm, blood oxygen levels, heart wall motion, and lung edema. It is desirable to provide ambulatory monitoring of CVP in heart failure patients for use in managing heart failure treatment.

DETAILED DESCRIPTION

In the following description, references are made to illustrative embodiments for carrying out the invention. It is understood that other embodiments may be utilized without departing from the scope of the invention. For purposes of clarity, the same reference numbers are used in the drawings to identify similar elements. Unless otherwise indicated, drawing elements are not shown to scale. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

Figure 1:
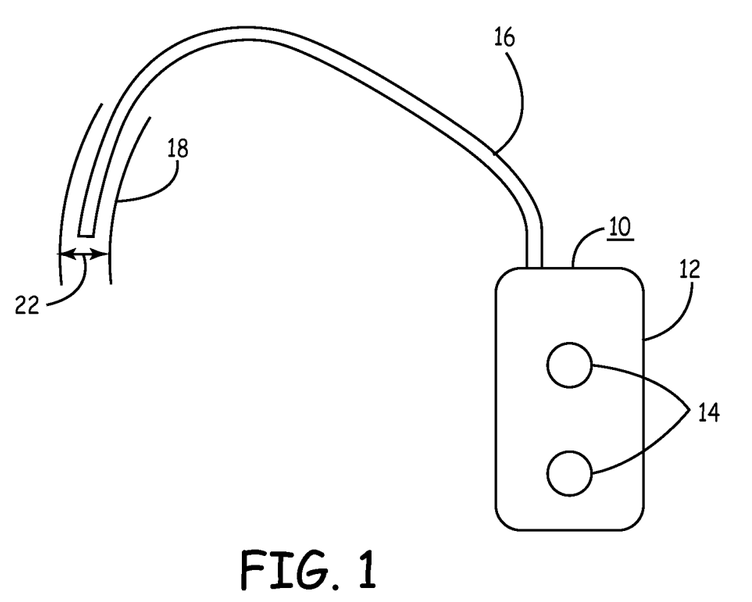
FIG. 1 is a schematic diagram of a patient monitoring system including an implantable medical device (IMD) coupled to a lead positioned within a vein in a patient's body.

FIG. 1 is a schematic diagram of a patient monitoring system including an implantable medical device (IMD) 10 coupled to a lead 16 positioned within a vein 18 in a patient's body. IMD 10 is at least capable of monitoring physiological signals and may include therapy delivery capabilities. IMD 10 may correspond to a variety of implantable medical devices including a cardiac pacemaker, implantable cardioverter defibrillator, implantable cardiac monitor, a drug pump, a neurostimulator or the like. Accordingly, IMD 10 may be coupled to additional leads or catheters operatively positioned relative to the patient's heart or other body tissues and carrying stimulating/sensing electrodes and/or other physiological sensors. While lead 16 is shown terminated within vein 18, it is recognized that lead 16 may be configured as a transvenous intracardiac lead that extends further into the patient's heart (not shown) for positioning electrodes or sensors within or near the heart.

In one embodiment, IMD 10 corresponds to an implantable monitor for sensing and recording ECG signals. ECG signals are sensed subcutaneously using electrodes 14 incorporated in the hermetically-sealed housing 12 of IMD 10. Housing 12 encloses circuitry included in IMD 10 for controlling device functions and processing sensed signals. As will be described in greater detail herein, lead 16 is provided with one or more sensors generating signals responsive to changes in the diameter 22 of vein 18. Such signals are used for monitoring or estimating CVP.

Figure 2:
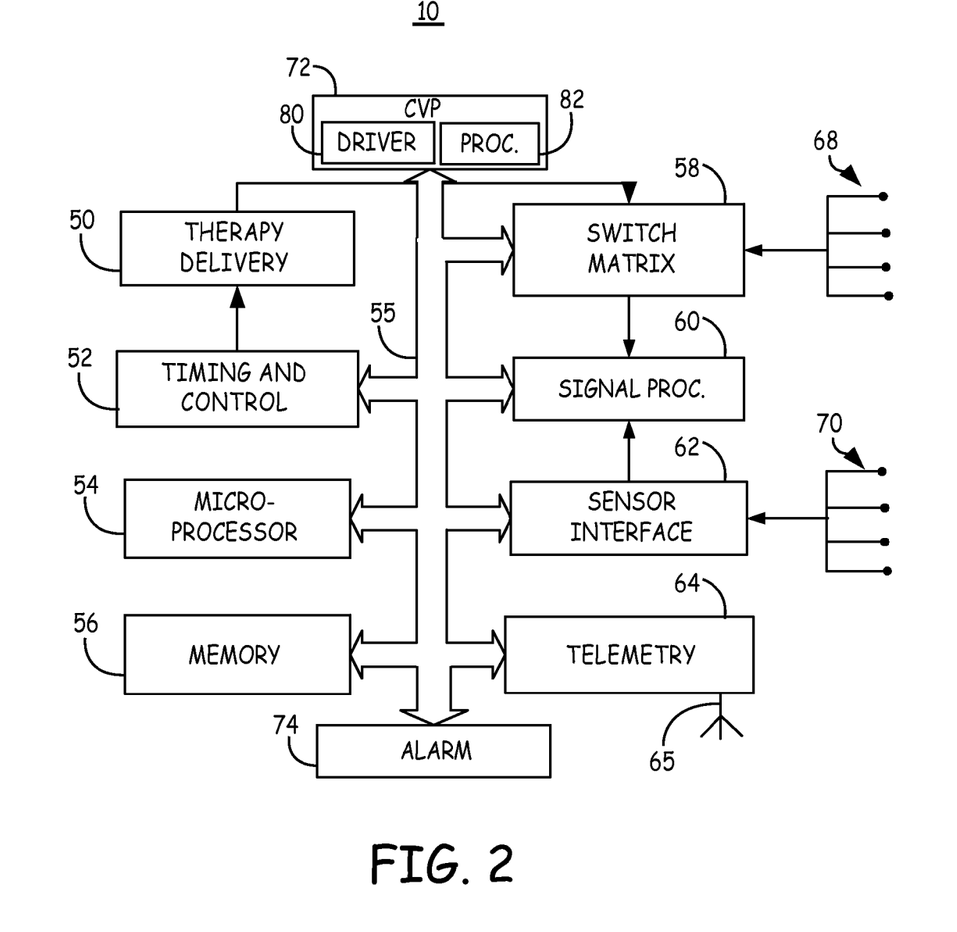
FIG. 2 is a functional block diagram of one embodiment of the IMD shown in FIG. 1.

FIG. 2 is a functional block diagram of one embodiment of IMD 10. IMD 10 generally includes timing and control circuitry 52 and an operating system that may employ microprocessor 54 or a digital state machine for timing sensing and therapy delivery functions (when present) in accordance with a programmed operating mode. Microprocessor 54 and associated memory 56 are coupled to the various components of IMD 10 via a data/address bus 55. IMD 10 includes therapy delivery module 50 for delivering a therapy in response to determining a need for therapy based on sensed physiological signals. Therapy delivery module 50 may provide drug delivery therapies or electrical stimulation therapies, such as cardiac pacing or arrhythmia therapies. Therapies are delivered by module 50 under the control of timing and control 52. Therapy delivery module 50 is typically coupled to two or more electrode terminals 68 via an optional switch matrix 58. Switch matrix 58 may be used for selecting which electrodes and corresponding polarities are used for delivering electrical stimulation pulses. Terminals 68 may be coupled to connectors providing electrical connection to electrodes 14 incorporated in IMD housing 12 (shown in FIG. 1) or other lead-based electrodes, including electrodes carried by lead 16 positioned in a vein for monitoring vein diameter as will be described herein.

Electrode terminals 68 are also used for receiving cardiac electrical signals. Cardiac electrical signals may be monitored for use in diagnosing or monitoring a patient condition or may be used for determining when a therapy is needed and in controlling the timing and delivery of the therapy. When used for sensing, electrode terminals 68 are coupled to signal processing circuitry 60 via switch matrix 58. Signal processor 60 includes sense amplifiers and may include other signal conditioning circuitry and an analog-to-digital converter. Electrical signals may then be used by microprocessor 54 for detecting physiological events, such as detecting and discriminating cardiac arrhythmias.

As will be described herein, electrical signals received at terminals 68 may be used for measuring a voltage or current signal for monitoring changes in vein diameter. In some embodiments, a voltage or current driver signal is applied to a pair of electrodes positioned in or on a vein and coupled via a conductor to terminals 68. The electrodes used for delivering the driver signal may be positioned a fixed distance apart. A voltage or current response signal is measured between the same or a different pair of electrodes. In one embodiment, the response signal is used to determine the impedance between the measuring electrodes. The measuring electrode pair may be positioned a fixed distance apart along a lead body portion that does not change shape as a result of vein distension. The impedance will vary with changes in vein diameter due to changes in the volume of blood surrounding the measuring electrodes. Alternatively, the measuring electrode pair may be positioned along a portion of the lead body configured to change in shape as the vein becomes distended, allowing the interelectrode distance to vary with changes in vein diameter. An impedance measurement will again vary with changes in the volume of blood surrounding the electrodes.

Alternatively, a voltage or current response signal is measured to compute a vein diameter based on an electrical vector measurement between triangulated electrodes. One pair of driver electrodes and one pair of measurement electrodes are selected from three triangulated electrodes. At least one of the driver pair and the measurement pair is positioned along a lead body portion that changes shape with changes in vein diameter. As a result, a measured response signal along the vector between the measurement electrode pair will vary with changes in vein diameter. As will be further described herein, the measured electrical vector provides a known parameter, along with the driver signal, for use in computing a vein diameter.

IMD 10 may additionally be coupled to one or more physiological sensors via physiological sensor terminals 70. Physiological sensors may include pressure sensors, accelerometers, flow sensors, blood chemistry sensors, activity sensors or other physiological sensors known for use with implantable devices. Physiological sensors may be carried by leads extending from IMD 10 or incorporated in or on the IMD housing 12. In particular, physiological sensors coupled to sensor terminals 70 may include an ultrasound transducer used in monitoring vein diameter as will be described herein.

Signals received at sensor terminals 70 are received by a sensor interface 62 which provides sensor signals to signal processing circuitry 60. Sensor signals are used by microprocessor 54 for detecting physiological events or conditions. In particular, signals from lead 16 are received for determining changes in vein diameter, which can be an indication of changes in CVP. A CVP module 72 may be implemented for generating driver signals delivered to driver electrodes via terminals 68 and receiving response signals measured between measurement electrodes via sensor interface 62 or signal processor 60. CVP module 72 is configured to execute algorithms for determining a relative change or level of CVP using the signal received from lead 16 operatively positioned relative to vein 18. CVP data is provided to microprocessor 54 and may be stored for use in diagnosing or monitoring the patient or for determining the need for delivering a therapy under control of the operating system.

Depending on the implementation of a vein diameter sensor, driver signals generated by CVP module 72 may include voltage or current signals injected for measuring impedance or measuring an electrical vector voltage or current signal. Alternatively, the driver signal generated by CVP module 72 may include an ultrasound signal. Likewise, a response signal received by CVP module 72 may include a voltage or current signal or an ultrasound signal. As such, CVP module 72 is shown to include driver circuitry 81 for generating driver signals under the control of timing and control module 52 and processing circuitry 82 for receiving and processing the response signal.

Microprocessor 70 and/or CVP module 72 may further receive a signal received at sensor terminals 70 and/or electrode terminals 68 that varies with respiration. A respiration signal may be used by microprocessor and/or CVP module 72 in conjunction with CVP data in a decision making process for detecting a heart failure condition. Alternatively, the respiration signal may be used in processing the vein diameter measurement signal to detect the presence of a respiration effect on vein diameter. A respiration signal may include an impedance signal or any other signal that varies with the respiration cycle.

The operating system includes associated memory 56 for storing a variety of programmed-in operating mode and parameter values that are used by microprocessor 54. The memory 56 may also be used for storing data compiled from sensed physiological signals and/or relating to device operating history for telemetry out on receipt of a retrieval or interrogation instruction. A CVP monitoring algorithm may be stored in memory 56 and executed by microprocessor 54 with input received from electrode terminals 68 and/or sensor terminals 70 for detecting a change in CVP. Alternatively, CVP module 72 may be embodied as dedicated circuitry for receiving and processing signals responsive to changes in vein diameter for use in monitoring CVP. Microprocessor 54 may respond to the CVP data by altering a therapy, triggering data storage, enabling other sensors for acquiring physiological data, or triggering alarm 74 to generate an alert signal to the patient or a caregiver that a serious condition has been detected that may require medical intervention. Data relating to CVP may be stored in memory 56 for later retrieval.

IMD 10 further includes telemetry circuitry 64 and antenna 65. Programming commands or data are transmitted during uplink or downlink telemetry between ICD telemetry circuitry 64 and external telemetry circuitry included in a programmer or monitoring unit. Telemetry circuitry 64 and antenna 65 may correspond to telemetry systems known in the art.

Figure 3A:
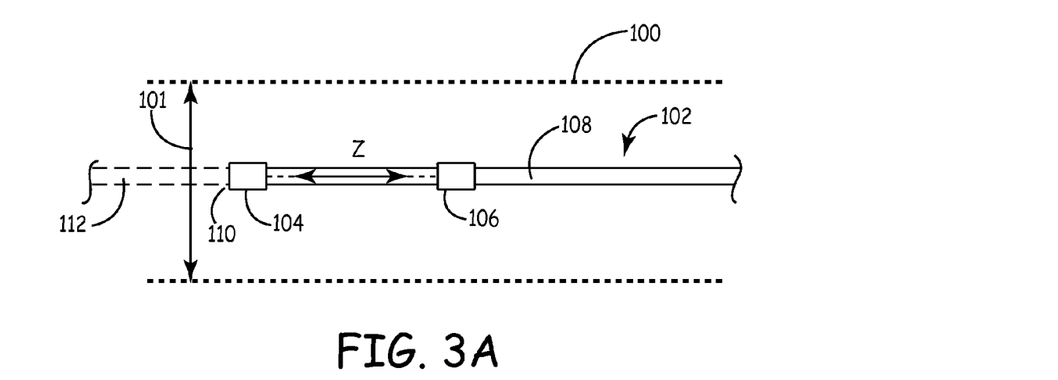
FIGS. 3A and 3B are schematic diagrams of embodiments of a transvenous lead that may be used for estimating vein diameter.
Figure 3B:
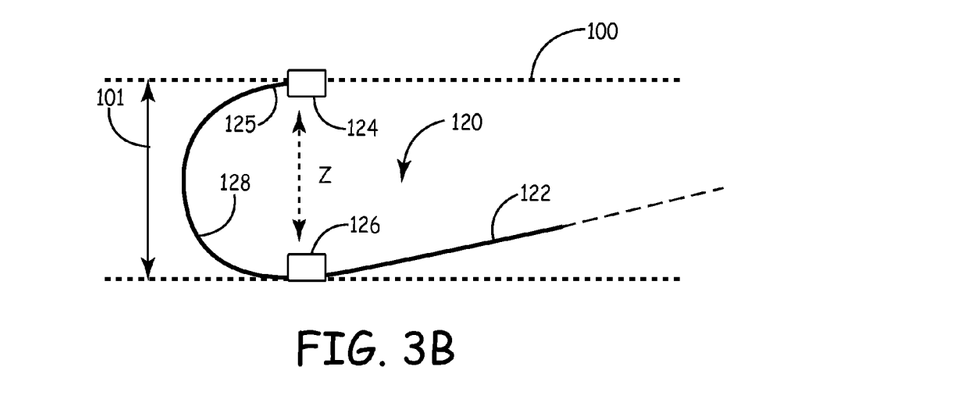

FIGS. 3A and 3B are schematic diagrams of embodiments of a transvenous lead that may be used for estimating vein diameter. In FIG. 3A, a lead 102 is advanced into a vein 100, which may be, for example, the superior vena cava, a subclavian vein, a jugular vein, or any other accessible vein. Lead 102 is shown as a substantially linear bipolar lead having a pair of electrodes 104 and 106 positioned along the lead body 108. Electrodes 104 and 106 are used to measure an interelectrode impedance Z that will vary with vein diameter 101. A known distance between electrodes 104 and 106 and a calibration procedure may be used for determining absolute values of vein diameter. Alternatively, relative changes in impedance may be determined for monitoring relative changes in vein diameter. As vein diameter 101 increases, the impedance measurement between electrodes 104 and 106 will decrease. Vein diameter 101 will increase with a rise in CVP which causes distension of vein 100. As such, relative changes in impedance measured between electrodes 104 and 106 will be inversely related to changes in CVP and can thus be used to estimate and detect changes in CVP.

Electrodes 104 and 106 may be located near a distal end 110 of lead 102. Specifically, electrode 104 may be a tip electrode positioned at or adjacent distal end 110 and electrode 106 spaced proximally from electrode 104. Alternatively, lead body 108 may include a distal portion 112, as indicated by dashed line, that extends distally from electrodes 104 and 106, further through vein 100. Electrodes 104 and 106 may be positioned at any location along a portion of lead body 108 that extends within vein 100. For example, lead 102 may be a transvenous intracardiac lead that extends further through the subclavian vein and into the patient's heart to position electrodes and/or other sensors in the heart. It is recognized that lead 102 can be embodied as a multi-polar lead including additional electrodes available for multiple impedance measurements in vein 100 along different vectors or locations within vein 100.

In FIG. 3B, lead 120 includes electrodes 124 and 126 positioned along a pre-formed curved portion 128 of lead body 122. Curved portion 128 is formed to position electrodes 124 and 126 substantially along a diameter 101 of vein 100, i.e. perpendicular to the longitudinal axis of vein 100. Curved portion 128 is shown formed substantially as an arc or semi-circle but could alternatively be formed as more of an angular bend. Curved portion 128 can be straightened when contained within a delivery guide catheter or when a guide wire (not shown) is advanced through lead body 122. Lead 122 can then be advanced to a desired position along vein 100 using the guide catheter or wire, curved portion 128 will regain its preformed curved shape when the guide catheter or guide wire is removed.

By positioning electrodes 124 and 126 substantially along a diameter of vein 100 rather than along a longitudinal axis of vein 100, impedance measurements between electrodes 124 and 126 may be more sensitive to changes in vein diameter 101 thus providing a more sensitive measurement for estimating CVP or detecting relative changes in CVP. Curved portion 128 is shown to have a radius that results in electrodes 124 and 126 positioned along opposite sides of the inner wall of vein 100.

Curved portion 128 is provided with a high compliance that allows portion 128 to change shape with changes in vein diameter, e.g. expand with increases in vein diameter that occur with elevated CVP. As vein diameter 101 increases, curved portion 128 expands or widens to maintain electrodes 124 and 126 against or near opposite sides of the inner vein wall. It is desirable to prevent distension of vein walls caused by preformed curved portion 128 pressing against the vein walls. Such distension of the vein walls by a preformed portion of the lead could cause an over-estimation of CVP. As such, the preformed portion 128 of the lead is provided with a low stiffness and high compliance relative to the vein wall to prevent stretching of the vein wall due to the lead geometry. In alternative embodiments, curved portion 128 may be formed small enough that electrodes 124 and 126 "float" within the lumen of vein 100 without making contact with both sides of the inner vein wall.

Curved portion 128 is shown in FIG. 3B to terminate the lead body 122 with electrode 124 provided at or adjacent distal lead body end 125, which forms the distal end of curved portion 128. In alternative embodiments, a preformed curved portion configured for positioning electrodes substantially along a diameter of vein 100 may be formed anywhere along the length of lead body 122.

Figure 3C:
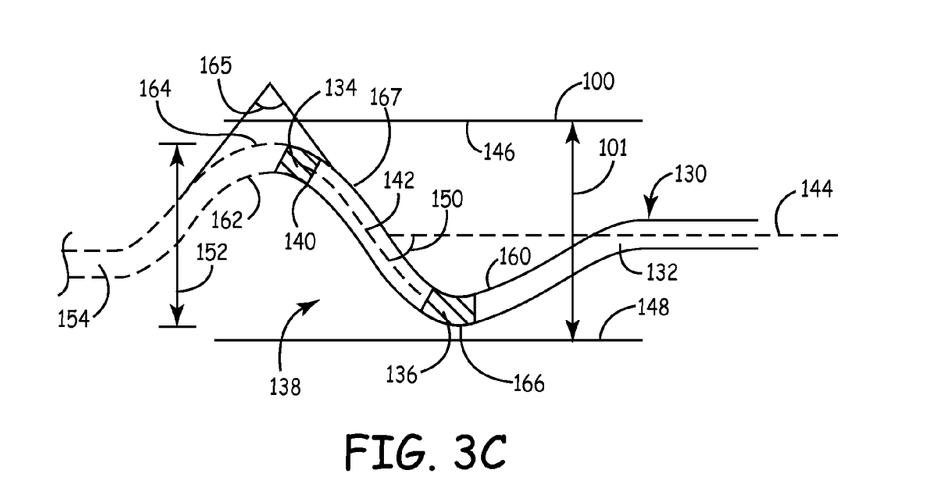
FIG. 3C is a plan view of a lead positioned in a vein and having a preformed portion for positioning electrodes away from a longitudinal axis of the vein.

FIG. 3C is a plan view of a lead 130 positioned in vein 100 and having a preformed portion 138 for positioning electrodes 134 and 136 away from a longitudinal axis 144 of vein 100. Preformed portion 138 is shown as generally "S" shaped thereby positioning one electrode 134 near one side 146 of the inner vein wall and the second electrode 136 near the opposite side 148 of the vein inner wall. The electrodes 134 and 136 are aligned along an axis 142 that extends at an angle 150 relative to a longitudinal axis 144 of vein 100. Preformed portion 138 is shown to have an outer diameter 152 formed by the maximum excursion of the curves included in portion 138 that is less than vein diameter 101. Preformed portion 138 will not cause distension of vein 100 by pressing against vein walls 146 and 148 and will therefore not cause erroneously high estimates of CVP.

Alternatively, preformed portion 138 may be formed with a high compliance and low stiffness relative to the vein wall and configured to position electrodes 134 and 136 against generally opposite sides 146 and 148 of the inner vein wall without causing distension of the vein wall. A preformed portion 138 may be more stably positioned at a desired location within the vein as compared to a generally straight lead. By positioning electrodes 134 and 136 at an angle 150 relative to longitudinal axis 144, impedance measurements between electrodes 134 and 136 might be more sensitive to changes in vein diameter 101 than measurements made by electrodes positioned along a longitudinal axis of vein 100.

In one embodiment, preformed curved portion 138 terminates at distal lead body end 140 with electrode 134 positioned at or adjacent distal end 140 and electrode 136 spaced proximally from distal end 140 and electrode 134. Alternatively, lead 130 may include a distal portion 154 that extends from preformed curved portion 138 as indicated by dashed line. In this embodiment, electrodes 134 and 136 are positioned along curved portion 138 which is preformed along any portion of lead body 130 that is positioned within vein 100.

Preformed portion 138 includes two curves or bends 160 and 162 separated by a relatively straight portion 167. Curves 160 and 162 may be formed with an angle 165 that results in a "relaxed" S-shape and a relatively small angle 150 formed between longitudinal axis 144 and electrode axis 142. The apex 164 of curve 162 and apex 166 of curve 160 are shown directed generally outward, in a radial direction with respect to vein longitudinal axis 144, toward opposing sides 146 and 148 of the inner vein wall. Alternatively, angle 165 may be formed as a more acute angle, resulting in a "tighter" S-shape and relatively larger angle 150 between electrode axis 142 and vein longitudinal axis 144.

Figure 3D:
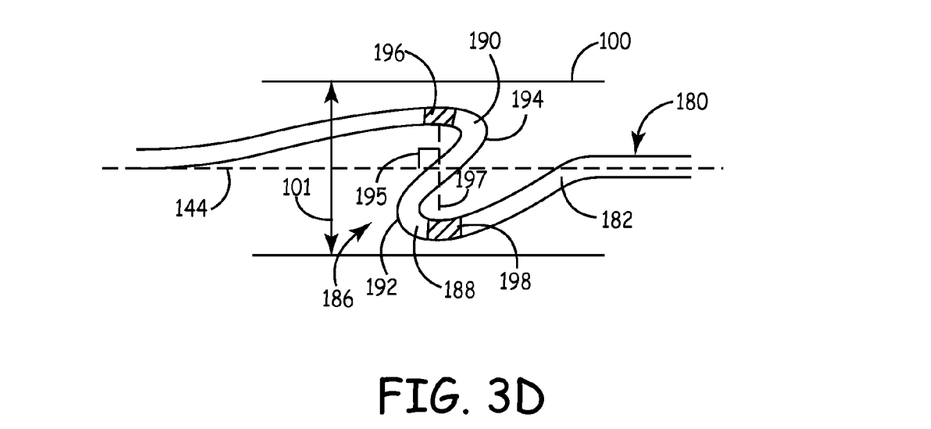
FIG. 3D is a plan view of a lead having a generally S-shaped preformed portion for carrying a pair of electrodes for use in monitoring vein diameter by measuring impedance.

In FIG. 3D, a lead 180 is shown having an alternative embodiment of a generally S-shaped preformed portion 186 carrying a pair of electrodes 196 and 198 for measuring impedance. Preformed portion 186 includes two curves or bends 188 and 190 each having an apex 192 and 194 that are directed in a generally longitudinal direction with respect to vein 100. In particular, apex 192 is directed in a generally distal direction and apex 194 is directed in a generally proximal direction resulting in electrodes 196 and 198 being arranged along an axis 197 that is substantially perpendicular to longitudinal axis 144 of vein 100 at angle 195. Electrodes 196 and 198 are shown adjacent to curves 190 and 188, respectfully, but may be located along the apexes 194 and 192 of curves 190 and 188, respectfully, or at any other location along preformed portion 186. It is recognized that one having skill in the art and the benefit of the teachings provided herein may readily conceive other preformed shapes that can be formed along a lead body for carrying impedance measuring electrodes along an axis that extends at an angle from a longitudinal axis of the vein within which the lead body extends. The electrode axis may extend along any angle between 0 and 90 degrees relative to the longitudinal axis 144 of vein 100.

It is recognized that electrodes positioned on a transvenous lead for measuring vein diameter, may also be selected as sensing electrodes for use in monitoring ECG signals. For example, ECG signals can be sensed between electrodes positioned on the transvenous lead or sensing vectors may be selected that include a transvenous lead electrode and any other electrode available, such as electrodes incorporated on the IMD housing as shown in FIG. 1. It is further recognized that electrodes positioned on a transvenous lead for measuring vein diameter may be used in measuring thoracic impedance for obtaining a respiration signal. The respiration signal may be used in conjunction with vein diameter measurements for monitoring changes in vein diameter due to respiration as will be further described below.

Figure 4:
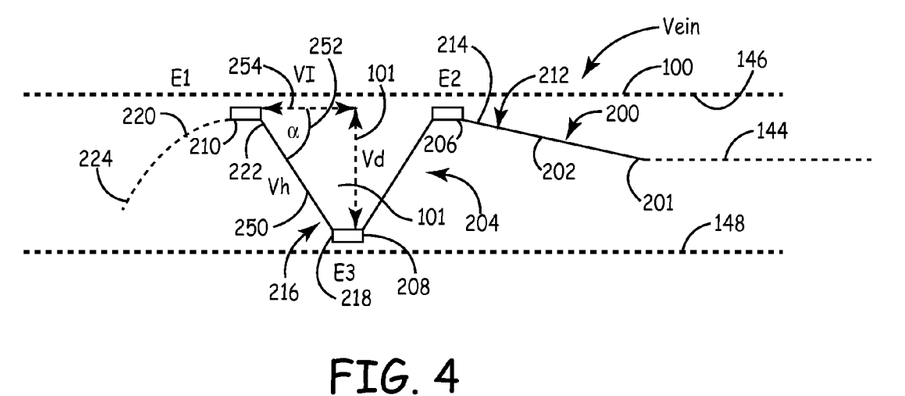
FIG. 4 is a plan view of another embodiment of a lead used for monitoring vein diameter.

FIG. 4 is a plan view of another embodiment of a lead 200 used for monitoring vein diameter. Lead 200 is advanced within vein 100 and includes a preformed curved portion 204 carrying three electrodes 206, 208 and 210 arranged in a substantially triangular configuration when preformed curved portion 204 takes its natural preformed shape. As will be described herein, electrodes 206, 208 and 210 are positioned for making electrical vector measurements for use in estimating vein diameter 101. In one embodiment, preformed portion 204 includes an initial bend or curve 201 that directs lead body 202 away from a longitudinal axis 144 toward one side 146 of the inner wall of vein 100. A second curve or bend 212 directs lead body 202 back toward the longitudinal axis 144 and toward the opposite side 148 of the vein inner wall. A third curve or bend 216 directs lead body 202 back toward the longitudinal axis 144 and toward the first side 146 of vein 100. The apexes 214 and 218 of curves 212 and 216, respectfully, are shown directed radially outward toward the vein inner wall.

A first electrode 206 is positioned at or adjacent apex 214 of the second curve 212, and a second electrode 208 is positioned at or adjacent apex 218 of third curve 216. A third electrode 210 is positioned at the distal end 222 of lead body 202. Distal end 222 terminates the preformed portion 204. Alternatively, lead body 202 may include a distal portion 224 extending from preformed portion 204 in which case a fourth curve or bend 220 is included. The third electrode 210 is positioned at or adjacent the apex of the fourth curve 220. The apex of fourth curve 220, when present, is also shown directed outward, toward the inner vein wall, in a generally radial direction. Preformed portion 204 is shown having a generally planar geometry such that electrodes 206, 208 and 210 are arranged triangularly in a plane in which electrodes 206 and 210 are positioned along one side 146 of the inner vein wall and intervening electrode 208 is positioned along an opposite side 148 of the inner vein wall.

Alternatively, preformed portion 204 may be a three-dimensional structure such that each of the three electrodes 206, 208 and 210 are each directed toward different sides of the vein inner wall. Such an arrangement is shown for example by the end view in FIG. 5. Lead 300 includes a three-dimensional preformed curved portion 304 positioning electrodes 306, 308 and 310 in a triangular arrangement for making electrical vector measurements for estimating vein diameter 101 of vein 100.

Figure 5:
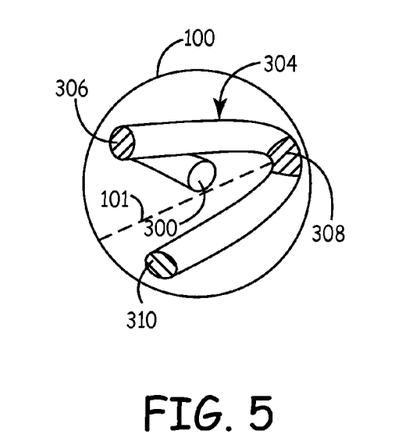
FIG. 5 is an end view of a lead including a three-dimensional preformed curved portion positioning electrodes in a triangular arrangement for making electrical measurements for estimating vein diameter.

Referring again to FIG. 4, and as similarly applies to lead 300 of FIG. 5, an electrical pulse may be applied between one of electrodes 206 and 210 and the intermediate electrode 208 positioned opposite electrodes 206 and 210. For example, an electrical pulse Vh 250 may be applied between electrodes 208 and 210. The projection Vi 254 of the electrical pulse Vh 250 is measured between the electrodes 206 and 210. The angle α 252 and the vein diameter 101 can be estimated by solving the following set of equations:

$$Vd = Vh * \sin \alpha$$

$$Vi = Vh * \cos \alpha$$

$$Vd = Vi * \tan \alpha$$

wherein Vh and Vi are known as the applied voltage Vh 250 between electrodes 208 and 210 and the measured voltage Vi 254 between electrodes 206 and 210, respectfully. By forming preformed portion 204 with a high compliance relative to the vein wall, preformed portion 204 will change shape with changes in vein diameter without itself causing distension of vein 100. The angle α 252 will change as the vein diameter 101 changes in response to changes in CVP.

Figure 6A:
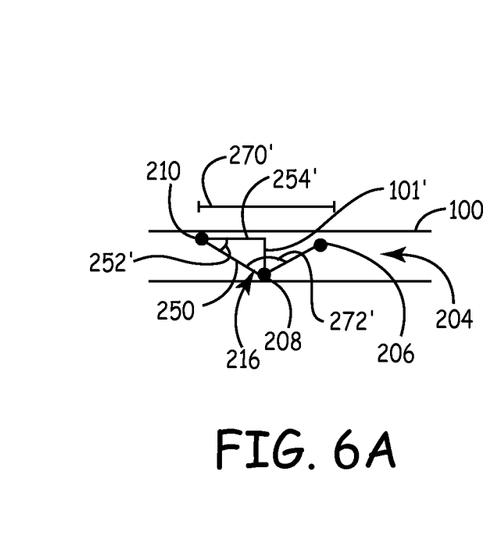
FIGS. 6A through 6C illustrate changes in vein diameter and resulting changes in preformed lead portion carrying triangulated electrodes.
Figure 6B:
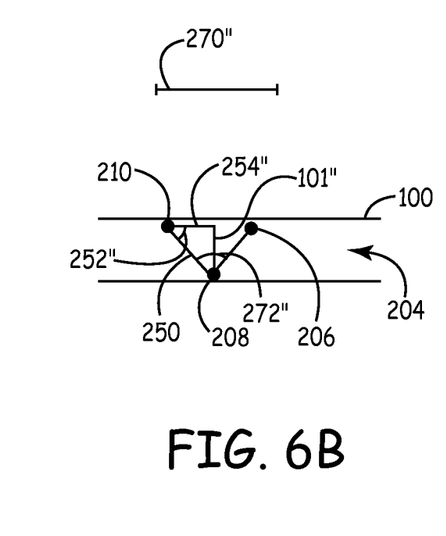
Figure 6C:
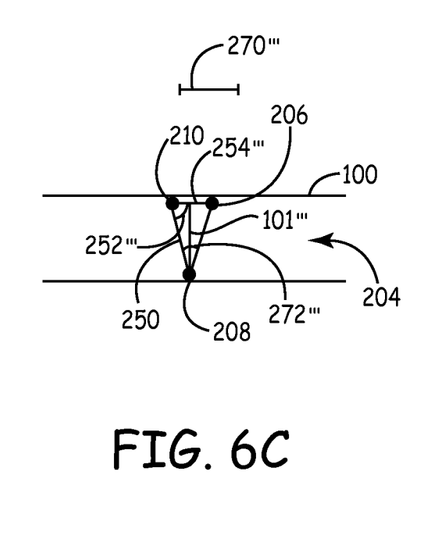

FIGS. 6A through 6C illustrate changes in vein diameter 101 and resulting changes in the angle α which can then be computed based on the applied and measured voltages Vh and Vi between the triangulated electrodes 206, 208 and 210. In one embodiment, electrodes 206, 208 and 210 are positioned at equidistant intervals along lead 200 (shown in FIG. 4). As shown in FIG. 6A relative to the illustration of 6B, as the vein diameter 101' becomes smaller than vein diameter 101", the curved portion 204 of lead 200 becomes "flattened" and the angle 272' of the third curve 216 becomes larger or more obtuse compared to angle 272". As a result, the distance 270' between electrodes 206 and 210 increases compared to the distance 270" and the angle α 252' becomes smaller or more acute compared to the angle α 252". The measured electrical vector Vi 254, which is the projection of the applied voltage signal Vh 250, will increase with a relative decrease in angle α 252' and corresponding decrease in vein diameter 101'.

With reference to FIG. 6C relative to FIG. 6B, as vein 100 becomes distended due to higher CVP, diameter 101''' becomes larger than diameter 101" allowing the curved portion 204 to become more tightly curved, i.e. a angle 272''' becomes smaller, bringing electrodes 206 and 210 closer together and causing angle α 252''' to become larger than angle α 252". As such, changes in CVP can be detected by computing the angle α 252 and diameter 101 using electrical measurements taken from triangulated electrodes. The measured electrical vector 254''' will be smaller than the corresponding vector 254" due to increasing vein diameter 101'''. Decreases in the measured electrical vector 254 results in a larger computed angle 252 and larger computed diameter 101.

Figure 7A:
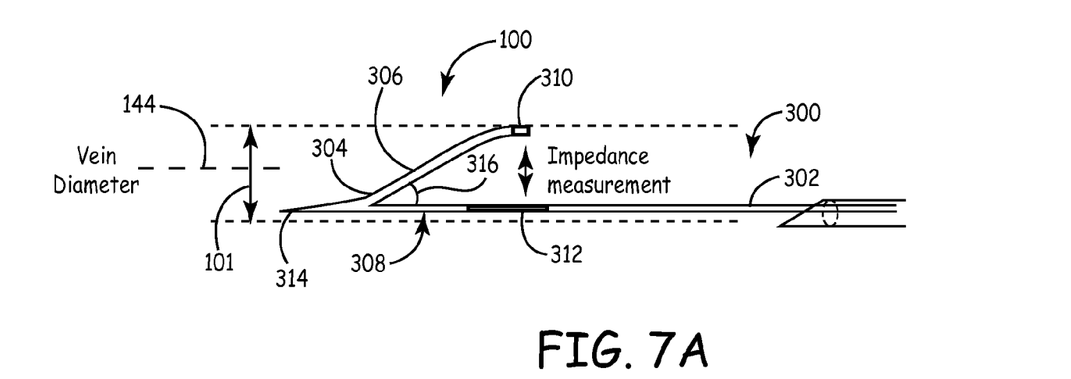
FIG. 7A is a partial plan view of yet another embodiment of a lead that may be used for monitoring vein diameter.

FIG. 7A is a plan view of yet another embodiment of a lead 300 that may be used for monitoring vein diameter. Lead 300 includes a lead body 302 having a bifurcation 304 from which a branch 306 extends off the main lead body 302. One electrode 312 is carried along the main lead body 302 and a second electrode 310 is carried by the branch 306. The bifurcated portion 308 is pre-formed to cause branch 306 to extend away from main lead body 302 to thereby position electrode 310 opposite electrode 312 along an axis substantially perpendicular to the longitudinal axis 144 of vein 100. An impedance measurement may be performed between electrodes 310 and 312 for use monitoring changes in vein diameter 101.

Bifurcation 304 is shown distal to electrode 312 along main lead body 302 such that branch 306 extends generally proximally to position electrode 310 opposite lead body 302. Alternatively, bifurcation 304 may be located proximal to electrode 312 such that branch 306 extends generally distally. Bifurcated pre-formed portion 308 may be at a distal end 314 of lead body 302. Alternatively, lead body 302 may extend beyond bifurcated portion 308 and carry additional sensors or electrodes distal to bifurcated portion 308.

Electrode 312 is shown having a greater longitudinal length than electrode 310. Electrode 310 will remain generally opposite electrode 312 when electrode 310 shifts longitudinally with respect to electrode 312 due to distension of vein 100. As vein diameter 101 changes, the angle 316 at which branch 306 extends from lead body 302 will change causing longitudinal shifts in the position of electrode 310. By providing electrode 312 as a longer electrode, electrode 310 will remain generally opposite a portion of electrode 312 with changes in vein diameter.

Figure 7B:
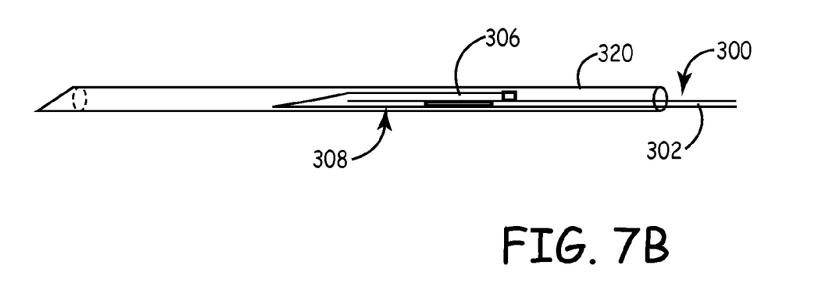
FIG. 7B is a partial plan view of the lead of FIG. 7A shown positioned in a guide catheter.

In FIG. 7B, lead 300 is shown positioned in a guide catheter 320 for delivering lead 300 to a desired venous site. When lead 300 is advanced through guide catheter 320, the bifurcated portion 308 will be retained in a generally straight configuration, with branch 306 held against lead body 302. When guide catheter 320 is removed, bifurcated portion 308 will regain its natural shape, positioning electrodes 310 and 312 against opposing sides of the inner vein wall.

Figure 7C:
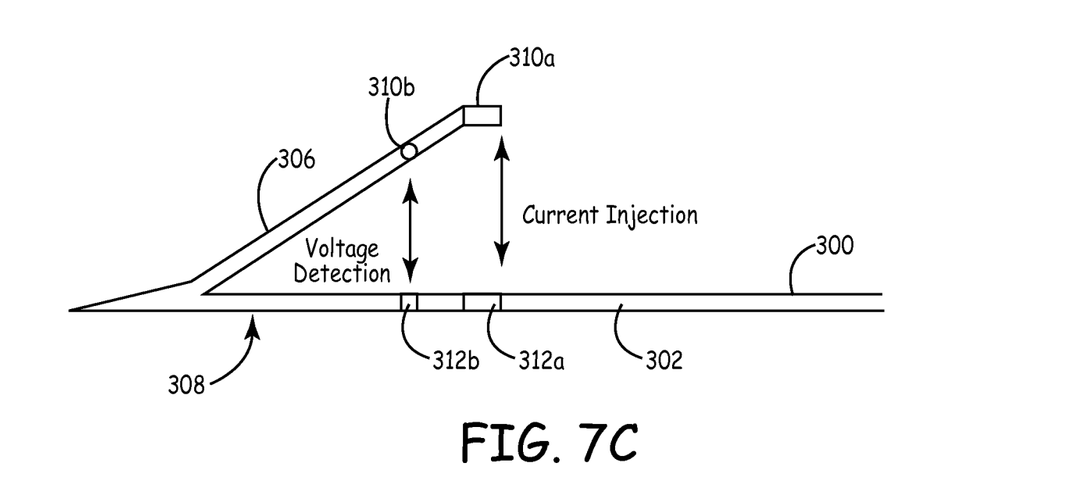
FIG. 7C is a partial plan view of a preformed bifurcated lead body portion according to an alternative embodiment of the invention.

FIG. 7C is a partial plan view of the preformed bifurcated portion 308 according to an alternative embodiment of the invention. Lead body 302 carries two electrodes 312a and 312b and branch 306 carries two opposing electrodes 310a and 310b. One opposing pair of electrodes 310a and 312a may be used to inject a current signal and the second pair of opposing electrodes 310b and 312b may be used for measuring the voltage signal for determining an impedance. Alternatively, the measured voltage signal may be used directly as an indication of vein diameter since the voltage signal will vary due to changes in the distance between electrode pairs 310a and 312a and 310b and 312b that occurs with changes in vein diameter.

Figure 7D:
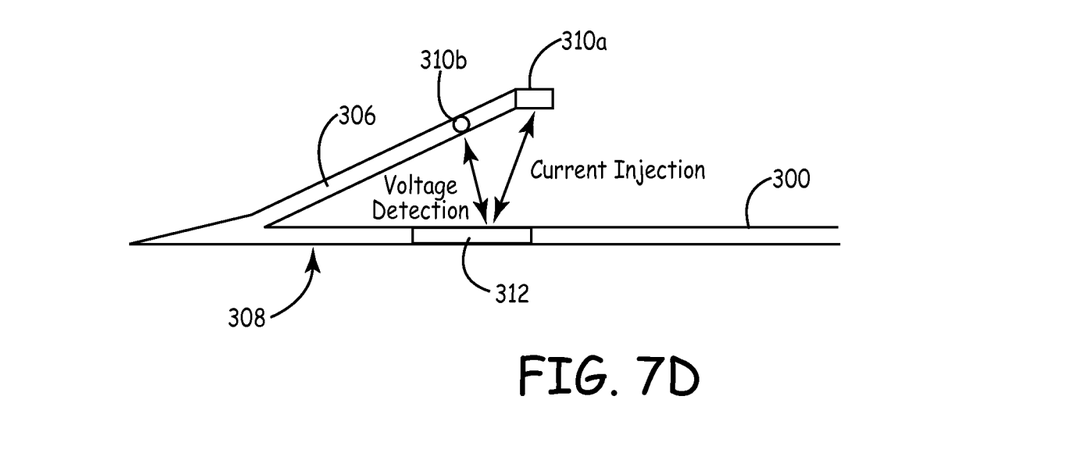
FIG. 7D is an alternative embodiment of a bifurcated lead for monitoring vein diameter.

FIG. 7D is an alternative embodiment of the bifurcated lead shown in FIG. 7C for monitoring vein diameter. In FIG. 7D, lead 300 includes a single electrode 312 along main lead body 302. Electrode 312 is provided with a length 313 that is greater than the length of either of the electrodes 310a and 310b carried along branch 306. The longer electrode 312 is used with electrode 310a for injecting a voltage or current signal and with electrode 310b, positioned in close proximity to electrode 310a, for detecting the voltage signal in response to the injected signal. The large surface area of the longer electrode 312 will reduce the effect of impedance at the tissue-electrode interface on the measured response signal. On the contrary, the small surface area of the electrode 310a may result in an impedance at the tissue-electrode interface that does have an impact on the response measurement. To reduce this effect, the response signal may be detected using a different electrode 310b than electrode 310a used to inject the driver signal.

Figure 8A:
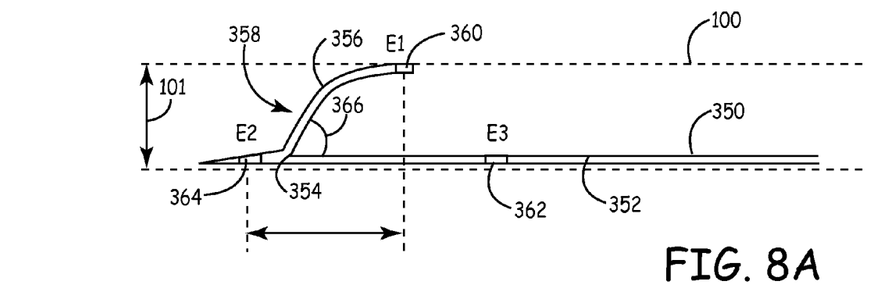
FIGS. 8A and 8B show an alternative embodiment of a bifurcated lead for use in monitoring vein diameter using electrical vector measurements.

FIG. 8A is an alternative embodiment of a bifurcated lead for use in monitoring vein diameter. Lead 350 includes a preformed bifurcated portion 358 having a branch 356 extending away from lead body 352 and carrying an electrode 360. Lead body 352 carries one electrode 362 proximal to bifurcation 354 and a second electrode 364 distal to bifurcation 354. The second electrode 364 may alternatively be located proximal to bifurcation 354 but distal to electrode 362. Electrodes 360, 362 and 364 are triangulated to allow for electrical vector measurements to be used for estimating vein diameter 101 as described previously. A voltage or current pulse is applied between electrode 360 and electrode 364. A voltage signal measured between electrode 364 and electrode 362 will be the projection of the applied voltage signal along the vector between electrodes 360 and 364. The measured voltage signal will vary as the angle 366 varies due to changes in vein diameter 101.

Figure 8B:
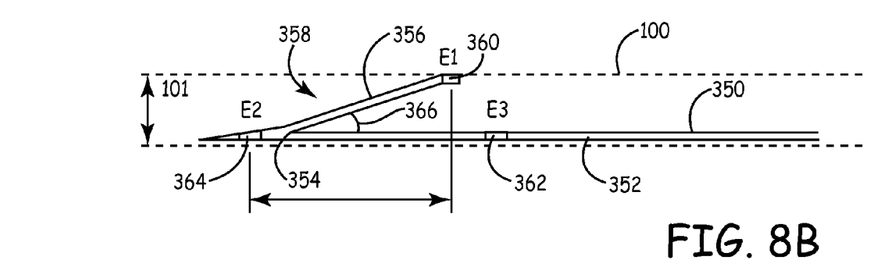

As shown in FIG. 8B, a smaller vein diameter 101 results in a smaller angle 366 between branch 356 and lead body 352. The measured voltage signal between electrodes 364 and electrodes 362 will change inversely proportionally with changes in the distance between electrodes 360 and 362.

Figure 9A:
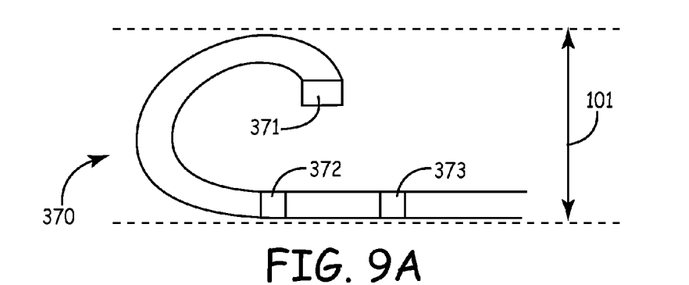
FIGS. 9A and 9B show an alternative lead configuration including a generally circular, or "pig tail", pre-formed portion carrying three electrodes for making electrical vector measurements.
Figure 9B:
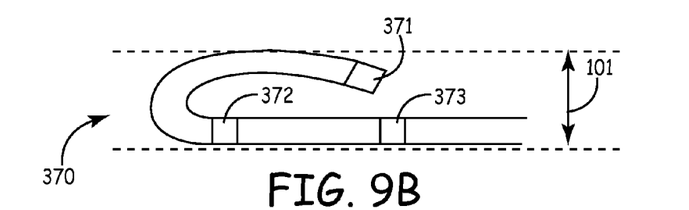

It is recognized that numerous geometries may be conceived for implementing preformed lead body portions carrying electrodes for measuring impedance or for measuring electrical vectors for monitoring changes in vein diameter. For example, an alternative configuration including a generally circular, or "pig tail", pre-formed portion 370 carrying three electrodes 371, 372 and 373 for making electrical vector measurements is shown in FIGS. 9A and 9B. As the vein becomes distended, preformed portion 370 takes on a more circular shape as shown in FIG. 9A as compared to the relatively more flattened shape shown in FIG. 9B. The projection of an applied electrical signal between electrodes 371 and 372 measured between electrodes 372 and 373 will change with changes in vein diameter. Changes in vein diameter cause a shape change of pre-formed portion 370 such that the relative distance between electrodes 371 and 372 positioned within vein 100 changes proportionally.

Figure 10A:
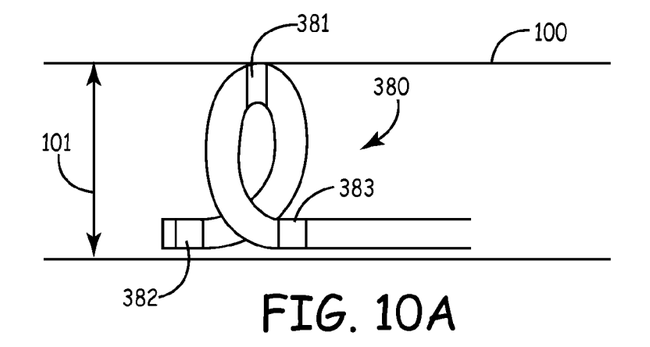
FIGS. 10A and 10B illustrate a helical or "corkscrew" pre-formed lead portion carrying three electrodes for measuring electrical vectors for vein diameter monitoring.
Figure 10B:
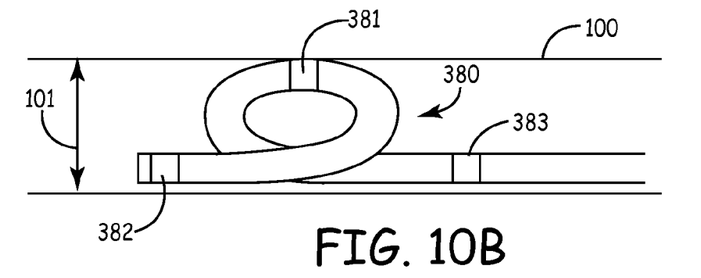

FIGS. 10A and 10B illustrate a helical or "corkscrew" pre-formed portion 380 carrying three electrodes 380, 381 and 382 for measuring electrical vectors. As vein diameter 101 decreases, the relative distance between electrodes 381 and 382 will change resulting in variations of the voltage signal measured between electrodes 382 and 383 in response to a signal applied between electrodes 381 and 382.

It is further recognized that while numerous embodiments described herein relate to a transvenous lead carrying electrodes positioned within the lumen of a vein, alternative embodiments could be adapted for placement of one or more electrodes or other sensors in extra-luminal positions, i.e., along the outer wall of the targeted vein. For example, a bifurcated or coiled lead portion could be positioned around a vein to position electrodes along the outer vein wall.

Figure 11:
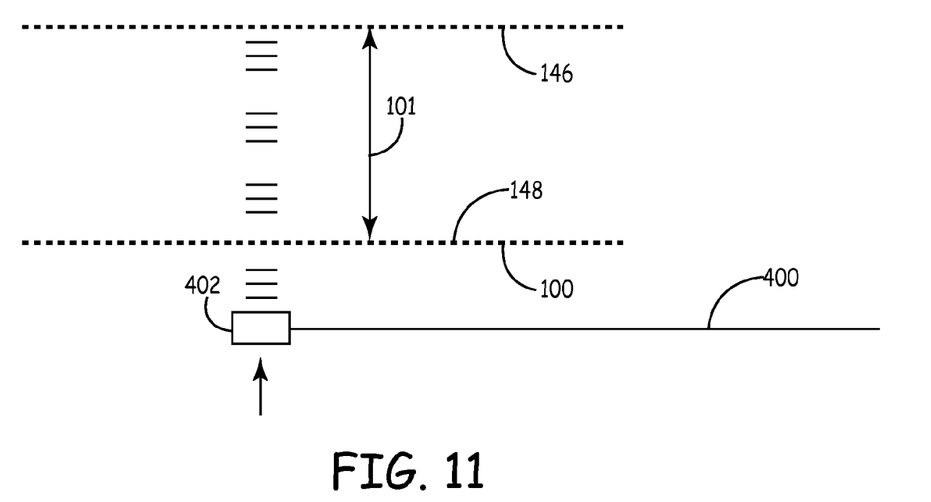
FIG. 11 is a plan view of yet another embodiment of a lead that may be used for monitoring vein diameter.

FIG. 11 is a plan view of yet another embodiment of a lead 400 that may be used for monitoring vein diameter. Lead 400 includes an ultrasound transducer 402 positioned along one side 148 of the wall of vein 100 and can be used for measuring vein diameter 101 using ultrasound techniques. Timing and control circuitry within an associated IMD provide the control signals for causing transmission and reception of ultrasound signals which are then used for estimating a diameter 101 based on the reflection of ultrasound waves 101 from the opposite side 146.

Figure 12:
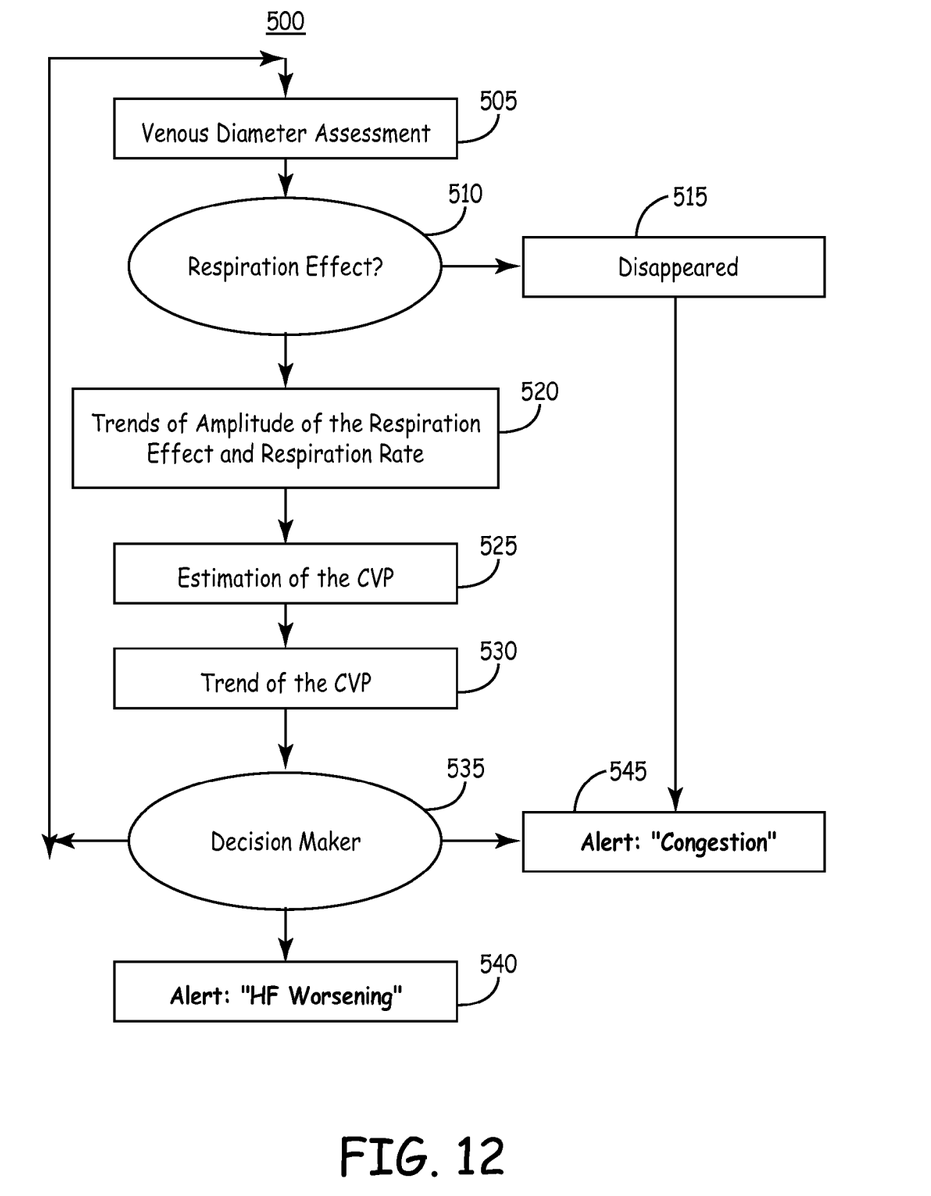
FIG. 12 is a flow chart of a method for monitoring CVP based on vein diameter measurements.

FIG. 12 is a flow chart of a method for ambulatory monitoring of CVP based on monitoring vein diameter using an implantable medical lead. Flow chart 500 is intended to illustrate the functional operation of the device, and should not be construed as reflective of a specific form of software or hardware necessary to practice the invention. It is believed that the particular form of software will be determined primarily by the particular system architecture employed in the device and by the particular detection and therapy delivery methodologies employed by the device. Providing software to accomplish the present invention in the context of any modern IMD, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 505, a venous diameter assessment is made. The venous diameter assessment may include one or more sequential measurements of vein diameter using any of the methods described herein, including electrical vector measurements, impedance measurements, and ultrasound measurements. The vein diameter assessment at block 505 may be performed in response to a user-generated command, on a scheduled periodic basis, or on a triggered basis in response to other measurements made by the IMD indicating heart failure monitoring should be performed.

At block 510, the vein diameter measurements are analyzed to determine if a cyclical effect of respiration is present. When CVP falls into a normal range, vein diameter varies with the respiration cycle. When CVP becomes very high, veins become highly distended. The modulation of vein diameter with respiration disappears due to highly distended veins. As such, if no respiration effect on vein diameter is found, as declared at block 515, the IMD detects a serious condition of congestive heart failure at block 545. The IMD may respond to this detection by generating an alert signal to the patient or to a clinician, or alter or initiate a therapy.

The respiration effect evaluated at block 510 may involve an analysis of the vein diameter measurements alone without sensing a respiration signal. For example, the vein diameter measurements may be performed at a sampling rate that allows recognition of the cyclical change in vein diameter with a respiration cycle. Vein diameter measurements may be performed, for example, at a rate of about 8 to 32 Hz. Vein diameter measurements may be performed for a period of several seconds up to, for example, one minute in order to obtain data points over at least one or several respiratory cycles. The vein diameter maximum and minimum measurements and/or time intervals between maximum and minimum measurements may then be evaluated to determine if the time intervals correspond to an expected respiratory cycle length and if a difference between the maximum and minimum reaches an expected modulation in vein diameter due to respiration. If the difference between the maximum and minimum is less than some predefined threshold, and/or the time intervals do not correspond to an expected respiration cycle period, the respiration effect is determined to have disappeared at block 515.

Alternatively, a respiration signal, such as a thoracic impedance signal or other signal known to vary with respiration, including the baseline of a sensed ECG signal, may be evaluated to identify the onset and length of respiration cycles. Examples of methods for acquiring a respiration signal are generally disclosed, for example, in U.S. Pat. No. 5,020,541 (Marriot), U.S. Pat. No. 6,752,765 (Jensen, et al.) and U.S. Pat. No. 7,160,252 (Cho, et al.), all of which patents are incorporated herein by reference in their entirety. The respiration signal may be used to set a "window", which corresponds to a respiration cycle, for evaluating the vein diameter measurements. For example, the onset and end of a respiration cycle may be identified from a respiration signal and the maximum and minimum vein diameter during the respiration cycle may be compared to determine if modulation of the vein diameter is present during that cycle. Alternatively, vein diameter measurements may be performed at the peak of inspiration and the peak of expiration and those measurements may be compared. It is recognized that numerous algorithms for detecting a respiratory effect on vein diameter may be conceived by one having skill in the art and the benefit of the teachings provided herein.

If the respiration effect on vein diameter is still detected at block 510, trends in the amplitude of the respiration effect are measured at block 520. For example, differences in a maximum and minimum vein diameter corresponding to peak expiration and peak inspiration may be stored and compared to previously stored measurements. The degree of modulation of vein diameter by respiration may show a decreasing trend with worsening heart failure. Vein diameter measurements used for tracking a trend of the respiration effect may be made on an hourly, daily, weekly or other predefined periodic basis. The respiration rate may be used in determining the respiration effect on vein diameter because the respiration cycle length may also affect the degree of modulation of vein diameter over the respiration cycle. As such, the trend in the amplitude of the respiration effect determined at block 520 may take into account the respiration rate measured at the time of the vein diameter measurements.

The CVP is estimated at block 525 using the vein diameter measurements. The CVP estimation may be computed as a function of one or more vein diameter measurements and/or the trend of the respiration effect on vein diameter. For example, a linear relationship between vein diameter and CVP may be assumed such that an estimated CVP change is determined to be directly proportional to a measured change in vein diameter. At block 530, a trend of the estimated CVP is evaluated by comparing the estimated CVP, or change in CVP, to previous CVP estimations. At block 535, the estimated CVP and the trend in CVP are evaluated. If the estimated CVP and the trend in CVP indicate an increase in CVP associated with worsening heart failure, an alert and/or therapy response is provided at block 540. If the estimated CVP and trend in CVP is determined to be severe, a congestive heart failure response may be provided at block 545. As such, at block 535, the estimated CVP and trend in CVP may be compared to predefined thresholds for determining the severity of any changes in CVP and the appropriate IMD response.

A measured respiration rate may also be used in combination with the CVP information in detecting the heart failure condition at block 535. For example, if measurements are made during sleep or during a known resting state, an increased respiration rate compared to previous resting respiration rate is a further indication of worsening heart failure due to worsening thoracic congestion increases. In addition to an alert signal, therapy adjustments or other physiological condition detection thresholds adjustments may be made in response to detecting a heart failure condition.

Thus, a method and apparatus for ambulatory monitoring of CVP have been presented in the foregoing description with reference to specific embodiments. It is appreciated that various modifications to the referenced embodiments may be made without departing from the scope of the invention as set forth in the following claims.

The invention claimed is:

1. An implantable medical device system, comprising:
an implantable sensor comprising at least a pair of measurement electrodes, the implantable sensor configured to be operatively positioned within a vein and further configured to generate a sensor signal responsive to changes in a diameter of the vein, wherein the sensor signal comprises a signal measurable between the pair of measurement electrodes;
timing and control circuitry configured to deliver a driver signal to the sensor to enable the sensor to generate the sensor signal; and
a processor configured to receive the sensor signal, and configured to determine a diameter of the vein in response to the sensor signal and to estimate a central venous pressure (CVP) based upon the vein diameter.

2. The system of claim 1 further comprising an elongated lead body carrying the sensor, the lead body comprises a preformed portion for positioning the sensor relative to a vein wall within the vein, wherein the preformed portion comprises a preformed shape such that after any shape changing forces acting on the preformed portion are removed the preformed portion will move toward regaining its preformed shape, the sensor being positioned along the preformed portion.

3. The system of claim 2 wherein the preformed portion having a high compliance and low stiffness relative to the vein wall such that the preformed portion when in contact with a vein wall of the vein will change shape with a change in vein diameter without causing distension of the vein.

4. The system of claim 2 wherein the preformed portion comprises a bifurcation and a branch extending from the bifurcation away from the elongated lead body, wherein the branch extending from the bifurcation comprises at least one electrode and further wherein the elongate lead body comprises at least one electrode of the measurement electrode pair.

5. The system of claim 2 wherein the sensor signal comprises a signal measurable between at least a pair of measurement electrodes of the sensor representative of impedance between the measurement electrode pair, the impedance being representative of vein diameter.

6. The system of claim 1 wherein the sensor comprises an ultrasound transducer and the signal comprises an ultrasound signal.

7. The system of claim 3 wherein the sensor comprises a first electrode, a second electrode and a third electrode positioned along the preformed portion in a triangular relationship to each other;
wherein the driver signal comprises a voltage signal applied between the first electrode and the second electrode of a driver electrode pair;
wherein the sensor signal is a voltage signal measured between the second electrode and the third electrode of the measurement electrode pair;
wherein the processor is configured to compute the vein diameter in response to the measured voltage; and
wherein a distance between one of the driver electrode pair and the measurement electrode pair changes in response to a change in shape of the preformed portion resulting from a change in vein diameter.

8. The system of claim 1 wherein the processor determining the vein diameter determines a change in vein diameter corresponding to a respiratory cycle.

9. The system of claim 8 further comprising a respiration sensor generating a signal responsive to respiration, the processor further being configured to detect the respiratory cycle.

10. The system of claim 8 wherein the processor detects congestive heart failure in response to a change in vein diameter corresponding to the respiratory cycle being absent.

11. The system of claim 8 wherein estimating the central venous pressure comprises determining a trend in the change in vein diameter corresponding to a respiratory cycle.

12. The system of claim 11 wherein the processor being further configured to determine a respiration rate and wherein the trend in the change in vein diameter corresponding to a respiratory cycle compares the respiration rate to the change in vein diameter.

13. The system of claim 1 wherein the processor being further configured to determine a trend in the estimated CVP.

14. The system of claim 13 wherein the processor being further configured to detect a worsening heart failure condition in response to the estimated central venous pressure and the trend in the estimated CVP.

15. An implantable medical device system for monitoring central venous pressure (CVP), comprising:
a transvenous lead comprising a preformed portion having a high compliance and low stiffness relative to a vein in which the transvenous lead is positioned such that the preformed portion when in contact with a vein wall of the vein will change shape with a change in vein diameter without causing distension of the vein, wherein the preformed portion comprises a preformed shape such that after any shape changing forces acting on the preformed portion are removed the preformed portion will move toward regaining its preformed shape, the preformed portion changing shape in response to a physiological change in the diameter of the vein wall;
a first electrode, a second electrode and a third electrode carried by the transvenous lead and positioned along the preformed portion in a triangular relationship;
timing and control circuitry configured to deliver a driver signal between a driver electrode pair comprising the first electrode and the second electrode;
a processor configured to measure a response signal between a measurement electrode pair comprising the second electrode and the third electrode, to compute a diameter of the vein in response to the measured response signal, to estimate CVP in response to the computed vein diameter, and to detect a heart failure condition in response to the estimated CVP, wherein a shape in change of the preformed portion changes a distance between at least one of the driver electrode pair and measurement electrode pair, and wherein the processor being further configured to determine a change in the computed vein diameter due to a respiration cycle and to determine a trend in the change in vein diameter due to respiration.

* * * * *